(12) United States Patent
Vedantham et al.

(10) Patent No.: US 9,629,597 B2
(45) Date of Patent: Apr. 25, 2017

(54) APPARATUS AND METHOD FOR X-RAY-BASED BREAST IMAGING

(71) Applicant: University of Massachusetts Medical School, Boston, MA (US)

(72) Inventors: Srinivasan Vedantham, Holden, MA (US); Andrew Karellas, Grafton, MA (US)

(73) Assignee: University of Massachusetts, Boston, MA (US)

( * ) Notice: Subject to any disclaimer, the term of this patent is extended or adjusted under 35 U.S.C. 154(b) by 78 days.

(21) Appl. No.: 14/772,227

(22) PCT Filed: Mar. 6, 2014

(86) PCT No.: PCT/US2014/021443
§ 371 (c)(1),
(2) Date: Sep. 2, 2015

(87) PCT Pub. No.: WO2014/138500
PCT Pub. Date: Sep. 12, 2014

(65) Prior Publication Data
US 2016/0000393 A1    Jan. 7, 2016

Related U.S. Application Data

(60) Provisional application No. 61/774,632, filed on Mar. 8, 2013.

(51) Int. Cl.
*A61B 6/00* (2006.01)
*A61B 6/04* (2006.01)
*A61B 6/02* (2006.01)
*A61B 6/03* (2006.01)

(52) U.S. Cl.
CPC ............... *A61B 6/502* (2013.01); *A61B 6/02* (2013.01); *A61B 6/04* (2013.01); *A61B 6/40* (2013.01); *A61B 6/4007* (2013.01); *A61B 6/4208* (2013.01); *A61B 6/4435* (2013.01); *A61B 6/4452* (2013.01); *A61B 6/461* (2013.01); *A61B 6/481* (2013.01); *A61B 6/485* (2013.01); *A61B 6/5211* (2013.01); *A61B 6/54* (2013.01); *A61B 6/025* (2013.01); *A61B 6/032* (2013.01)

(58) Field of Classification Search
CPC ......... A61B 6/022; A61B 6/025; A61B 6/032; A61B 6/035; A61B 6/0414; A61B 6/0435; A61B 6/4007; A61B 6/4014; A61B 6/4429; A61B 6/502
See application file for complete search history.

(56) References Cited

U.S. PATENT DOCUMENTS

| | | | | |
|---|---|---|---|---|
| 3,609,355 A | * | 9/1971 | Schwarzer | ............ A61B 6/502 378/180 |
| 5,386,447 A | * | 1/1995 | Siczek | ................ A61B 6/0414 378/196 |
| 5,872,828 A | * | 2/1999 | Niklason | ............... A61B 6/025 378/23 |

(Continued)

*Primary Examiner* — Thomas R Artman
(74) *Attorney, Agent, or Firm* — Milstein Zhang & Wu LLC

(57) ABSTRACT

The invention provides x-ray-based breast imaging systems and related methods that are, for example, applicable to contrast enhanced digital mammography and contrast enhanced digital breast tomosynthesis and allow fast, cost-effective and accurate x-ray imaging.

20 Claims, 8 Drawing Sheets

(56) References Cited

U.S. PATENT DOCUMENTS

| | | | | |
|---|---|---|---|---|
| 6,292,531 B1* | 9/2001 | Hsieh | .................. | A61B 6/02 |
| | | | | 378/22 |
| 7,649,981 B2* | 1/2010 | Seppi | .................. | A61B 6/032 |
| | | | | 378/124 |
| 7,676,021 B2* | 3/2010 | Tsujii | .................. | A61B 6/032 |
| | | | | 378/17 |
| 8,094,773 B2* | 1/2012 | Boese | .................. | A61B 6/025 |
| | | | | 378/21 |
| 8,194,819 B2* | 6/2012 | Eliasson | .............. | A61B 6/025 |
| | | | | 378/189 |
| 2005/0084073 A1* | 4/2005 | Seppi | .................. | A61B 6/032 |
| | | | | 378/156 |
| 2009/0080594 A1* | 3/2009 | Brooks | ................ | A61B 6/502 |
| | | | | 378/4 |
| 2010/0290585 A1* | 11/2010 | Eliasson | .............. | A61B 6/025 |
| | | | | 378/37 |
| 2016/0000393 A1* | 1/2016 | Vedantham | .......... | A61B 6/4208 |
| | | | | 378/27 |

* cited by examiner

APPARATUS AND METHOD FOR X-RAY-BASED BREAST IMAGING

PRIORITY CLAIMS AND RELATED PATENT APPLICATIONS

This application is the U.S. national phase of and claims priority to PCT/US14/21443, filed Mar. 6, 2014, which claims the benefit of priority from U.S. Provisional Application Ser. No. 61/774,632, filed on Mar. 8, 2013, the entire content of each of which is incorporated herein by reference in its entirety.

STATEMENT REGARDING FEDERALLY FUNDED RESEARCH OR DEVELOPMENT

The United States Government has certain rights to the invention pursuant to Grant Nos. R21 CA134128 and R01 CA128906 from the National Institutes of Health to the University of Massachusetts.

TECHNICAL FIELD OF THE INVENTION

The invention generally relates to x-ray-based imaging systems and methods. More particularly, the invention relates to x-ray breast imaging systems and related methods that are, for example, applicable to contrast enhanced digital mammography and contrast enhanced digital breast tomosynthesis.

BACKGROUND OF THE INVENTION

Early detection and accurate diagnosis of breast cancer with screening and diagnostic mammography are critical aspects of breast cancer treatment as they lead to early intervention in the course of the disease, possibly before the cancer has spread. Mammography has been the primary imaging tool for screening and diagnostic work-up of breast cancer. It is well known that the sensitivity of mammography is substantially reduced in radiographic dense breasts. Adjunctive use of breast magnetic resonance imaging (MRI) is recommended for screening women with high-risk of breast cancer.

MRI uses a magnetic field and pulses of radio wave energy to image breasts. MRI is able to provide different information than can be imaged with an x-ray based method such as mammography. Thus, breast MRI plays a major role in diagnostic imaging. Key factors that contribute to the high sensitivity of breast MRI include the ability to provide three-dimensional (3-D) images of the breast, and more importantly, the use of intravenously injected Gadolinium contrast media enhances abnormalities associated with hypervascularity or tumor angiogenesis. However, cost and access are major limitations for MRI tests. Also, breast MRI scans have much lower spatial resolution than mammography.

Since mammography provides a 2-D image of the 3-D breast, superposition of structures leads to anatomic noise, which can mask lesions and/or mimic the presence of lesions that can lead to additional imaging and tissue biopsy.

Digital breast tomosynthesis is a technique where a number of 2-D x-ray projections are acquired over a limited angular range not exceeding 180 degrees (typically from 15 to 60 degrees). The acquired images are mathematically reconstructed to provide a quasi-tomographic 3-D image of the object. (Niklason, et al. 1997 *Radiology* 205 (2), 399-406.) This technique has the potential to improve detection and diagnosis of an abnormality by reducing the masking effect of superposed anatomy. (Suryanarayanan, et al. 2000 *Acad Radiol* 7 (12), 1085-1097; Suryanarayanan, et al. 2001 *Acad Radiol* 8 (3), 219-224.) A clinical breast tomosynthesis system recently received marketing approval from the FDA. (Selenia® Dimensions®, Hologic Inc., Bedford, Mass.) However, mammography and digital breast tomosynthesis systems that are currently used provide only anatomic images of the breast.

The clinical potential is being investigated for contrast enhanced digital mammography and contrast enhanced digital breast tomosynthesis, wherein iodinated contrast media is intravenously injected. (Jong, et al. 2003 *Radiology* 228 (3), 842-850; Lewin, et al. 2003 *Radiology* 229 (1), 261-268; Chen, et al. 2007 *Acad Radiol* 14 (2), 229-238; Puong, et al. *Medical Imaging* 2008: *Physics of Medical Imaging* San Diego, Calif., 2008 *Proc. SPIE, Vol.* 6913, pp. 69130Z (62008); DOI:69110.61117/69112.770148; Saunders, et al. *Medical Imaging* 2008: *Physics of Medical Imaging* San Diego, Calif., 2008 Proc. SPIE, Vol. 6913, pp. 69130Y (62008); DOI:69110.61117/69112.772042.) A major limitation of existing systems for contrast enhanced digital mammography and contrast enhanced digital breast tomosynthesis require repositioning of the subject, as the system is designed to image one breast at a time. This may result in the need for two injections that double the amount of injected contrast media, for bilateral exams.

In PCT/US12/22936 (by Vedantham and Karellas, expressly incorporated herein by referenced for all purposes), a tomosynthesis imaging system was disclosed for providing radiographic, stereoscopic and tomographic images of an object, such as the human breast. The system includes a high-fluence rate x-ray source and a plurality of satellite x-ray sources operating at lower fluence rate than the high-fluence rate source. A controller controls the operation and locations of the sources, and the operation of a detector. The method provides procedures in which the operation of the high-fluence source and the satellite sources are individually controlled as to location and orientation relative to the object of interest. In some operations, one satellite source may be operating while another satellite source may be repositioning. By proper control, a reduced x-ray dose and reduced operating time can be attained.

While there have been several studies on dynamic contrast enhanced breast MRI, Boetes reported their results with a temporal sampling of 2.3 seconds. (Kuhl, et al. 2000 *J Magnetic Resonance Imaging* 12 (6), 965-974; Boetes, et al. 1994 *Radiology* 193 (3), 777-781.) Even with this relatively coarse temporal sampling, they observed that malignant lesions started to enhance 11.5 seconds after contrast administration. Applying this criterion, they achieved a sensitivity and specificity of 95% and 86% respectively, in a cohort of 87 lesions.

Contrast enhanced digital mammography has been studied either using dual-energy technique wherein low and high-energy image pairs are acquired after administration of contrast media, or using temporal subtraction wherein pre-contrast image is acquired before contrast administration and post-contrast image(s) after contrast administration. (Lewin, et al. 2003 *Radiology* 229 (1), 261-268.) In a study on contrast-enhanced dual-energy digital mammography by Lewin et al., low and high-energy images were acquired 150 seconds after administration of contrast media. This method provided a singular time-point on contrast enhancement and did not provide for studying contrast enhancement kinetics. While it is possible to acquire multiple images at different time points after contrast administration, the temporal resolution of such an approach is limited by the frame-rate capabilities of the x-ray imaging detector. In another study, the first image after the start of contrast administration is acquired at 1 minute and subsequent images are acquired in 2 minutes interval. (Jong, et al. 2003 *Radiology* 228(3), 842-850.) Thus, the technique presents coarse temporal sampling of contrast enhancement kinetics.

U.S. Pat. No. 8,194,819 B2 (Eliasson), a mammography method system was disclosed that utilized two x-ray detectors in parallel on opposite sides of the support unit (facing away from each other) to generate x-ray images of the breasts.

In a contrast enhanced digital breast tomosynthesis study, post contrast image acquisition began 90 seconds after contrast administration and each of the nine projection images used to reconstruct the quasi-tomographic image was separated by 30 seconds. (Chen, et al. 2007 *Acad Radiol* 14 (2), 229-238.) Thus, the method takes 4.5 minutes to acquire the dataset that represents a single time point and hence suffers from substantial limitations on studying contrast enhancement kinetics.

Thus, there remains an ongoing need for alternatives to breast MRI that are cost-effective and provide better spatial and temporal resolution for visualizing abnormalities in the breast.

SUMMARY OF THE INVENTION

The invention provides x-ray-based breast imaging systems and related methods that are, for example, applicable to contrast enhanced digital mammography and contrast enhanced tomographic imaging of the breast such as digital breast tomosynthesis or stereoscopic imaging and allow fast, cost-effective and accurate x-ray imaging. A unique aspect of the present invention is the use of a single x-ray detector in association with one or two x-ray sources or arrays of x-ray sources to generate fast and high-quality images of improved spatial resolution, all without the need to reposition the patient during the imaging procedure.

In one aspect, the invention generally relates to a system for generating x-ray images of breasts of a subject. The system includes: (1) a support for positioning a right and a left breast of the subject; (2) an assembly of an x-ray source and an x-ray detector; (3) a controller unit coupled to and command the operation of the x-ray source and the x-ray detector assembly; and (4) a computation unit configured to receive, analyze, display and/or store the one or more images of the right or the left breast. The x-ray source and the x-ray detector are configured to allow an x-ray beam generated by the x-ray source to pass through the right or the left breast of the subject and to project onto a detecting surface of the x-ray detector, positioned between the right and left breasts, to register one or more images of the right or the left breast; and wherein the assembly of the x-ray source and the x-ray detector is rotatable in synchrony around an axis located between the right and left breasts and normal to the subject's chest, and is translatable in one or more dimensions relative to the subject's chest. The assembly of the x-ray source and the x-ray detector is first positioned relative to one breast to allow the registration of one or more images thereof and is then positioned relative to the other breast to allow registration of one or more images of the other breast.

In another aspect, the invention generally relates to a system for generating x-ray images of breasts of a subject. The system includes: (1) a support for positioning a right and a left breast of the subject; (2) two arrays of x-ray sources, a right array and a left array positioned to image the right breast and the left breast, respectively, wherein the x-ray sources of each of the two arrays are arranged along a pre-defined trajectory; (3) an x-ray detector, positioned between the right and left breasts, configured to allow an x-ray beam generated by the right or the left array of x-ray sources to pass through the right or the left breast of the subject and to project onto a detecting surface of the x-ray detector to register one or more images of the right or the left breast; (4) a controller unit coupled to and command the operation of the x-ray detector; and (5) a computation unit configured to receive, analyze, display and/or store the one or more images of the right or the left breast. The x-ray detector is rotatable around an axis located between the right and left breasts and normal to the subject's chest, and is translatable in one or more dimensions relative to the subject's chest. The x-ray detector is first positioned relative to one breast to allow the registration of one or more images thereof and is then positioned relative to the other breast to allow registration of one or more images of the other breast.

In yet another aspect, the invention generally relates to a system for generating x-ray images of breasts of a subject. The system includes: (1) a support for positioning a right and a left breast of the subject; (2) two x-ray sources, a right and a left positioned to image the right breast and the left breast, respectively; (3) an x-ray detector, positioned between the right and left breasts, configured to allow an x-ray beam generated by the right or the left x-ray source to pass through the right or the left breast of the subject and to project onto a detecting surface of the x-ray detector to register one or more images of the right or the left breast; (4) a controller unit coupled to and command the operation of the x-ray detector; and (5) a computation unit configured to receive, analyze, display and/or store the one or more images of the right or the left breast. The x-ray detector is rotatable around an axis located between the right and left breasts and normal to the subject's chest, and is translatable in one or more dimensions relative to the subject's chest. The x-ray detector is first positioned relative to one breast to allow the registration of one or more images thereof and is then positioned relative to the other breast to allow registration of one or more images of the other breast.

In yet another aspect, the invention generally relates to a system for generating x-ray images of breasts of a subject. The system includes: (1) a support for positioning a right and a left breast of the subject; (2) an assembly of an array of one or more x-ray sources and an x-ray detector positioned on opposite sides of a breast of the subject to be imaged and configured to allow an x-ray beam generated by the array of one or more x-ray sources to pass through a breast of the subject and to project onto a detecting surface of the x-ray detector; (3) a controller unit coupled to and command the operation of the assembly of an array of one or x-ray sources and an x-ray detector; and (4) a computation unit configured to receive, analyze, display and/or store the one or more images of the right or the left breast. The assembly of the array of one or more x-ray sources and the x-ray detector is rotatable around an axis located between the x-ray source and the x-ray detector and normal to the subject's chest, and is translationally moveable along the axis. The assembly of the array of one or more x-ray sources and the x-ray detector is first positioned relative to one breast of the subject to allow the registration of one or more images thereof and is then positioned relative to the other breast of the subject to allow registration of one or more images thereof.

In yet another aspect, the invention generally relates to a system for generating x-ray images of breasts of a subject.

The system includes: (1) a support for positioning a right and a left breast of the subject; (2) an assembly of an array of one or more x-ray sources and an x-ray detector positioned on opposite sides of a breast of the subject to be imaged and configured to allow an x-ray beam generated by the array of one or more x-ray sources to pass through the breast of the subject and to project onto a detecting surface of the x-ray detector; (3) a controller unit coupled to and command the operation of the assembly; and (4) a computation unit configured to receive, analyze, display and/or store the one or more images of the right or the left breast. The assembly of the array of one or more x-ray sources and the x-ray detector is rotatable around an axis located between and below the subject's breasts and normal to the subject's chest; The assembly of the array of one or more x-ray sources and the x-ray detector is first positioned relative to one breast of the subject to allow the registration of one or more images thereof and is then positioned relative to the other breast of the subject to allow registration of one or more images thereof.

In yet another aspect, the invention generally relates to a system for generating x-ray images of breasts of a subject. The system includes: (1) a support for positioning a right and a left breast of the subject; (2) an assembly of an array of one or more x-ray sources and an x-ray detector positioned on opposite sides of a breast of the subject to be imaged and configured to allow an x-ray beam generated by the array of one or more x-ray sources to pass through the breast of the subject and to project onto a detecting surface of the x-ray detector; (3) a controller unit coupled to and command the operation of the assembly; and (4) a computation unit configured to receive, analyze, display and/or store the one or more images of the right or the left breast. The assembly of the array of one or more x-ray sources and the x-ray detector is rotatable around an axis located between and above the subject's breasts and normal to the subject's chest. The assembly of the array of one or more x-ray sources and the x-ray detector is first positioned relative to one breast of the subject to allow the registration of one or more images thereof and is then positioned relative to the other breast of the subject to allow registration of one or more images thereof.

In yet another aspect, the invention generally relates to a method for generating x-ray images of breasts of a subject. The method includes: (1) providing a support for positioning a right and a left breast of the subject; (2) providing an assembly of an x-ray source and an x-ray detector; (3) positioning the assembly of the x-ray source and the x-ray detector relative to one breast to allow the registration of one or more images thereof; (4) imaging the breast to register one or more images on the x-ray detector; (5) positioning the assembly of the x-ray source and the x-ray detector relative to the other breast to allow registration of one or more images of the other breast; and (6) imaging the other breast to register one or more images on the x-ray detector. The x-ray source and the x-ray detector are configured to allow an x-ray beam generated by the x-ray source to pass through the right or the left breast of the subject and to project onto a detecting surface of the x-ray detector, positioned between the right and left breasts, to register one or more images of the right or the left breast. The assembly of the x-ray source and the x-ray detector is rotatable in synchrony around an axis located between the right and left breasts and normal to the subject's chest, and is translatable in one or more dimensions relative to the subject's chest.

In yet another aspect, the invention generally relates to a method for generating x-ray images of breasts of a subject.

The method includes: (1) providing a support for positioning a right and a left breast of the subject; (2) providing two arrays of x-ray sources, a right array and a left array positioned to image the right breast and the left breast, respectively, wherein the x-ray sources of each of the two arrays are arranged along a pre-defined trajectory; (3) positioning an x-ray detector between the right and left breasts configured to allow an x-ray beam generated by the right or the left array of x-ray sources to pass through the right or the left breast of the subject and to project onto a detecting surface of the x-ray detector; (4) imaging the right or the left breast to register one or more images on the x-ray detector; (5) positioning an x-ray detector between the left and right breasts configured to allow an x-ray beam generated by the left or the right array of x-ray sources to pass through the left or the right breast of the subject and to project onto a detecting surface of the x-ray detector; and (6) imaging the left or the right breast to register one or more images on the x-ray detector.

In yet another aspect, the invention generally relates to a method for generating x-ray images of breasts of a subject. The method includes: (1) providing a support for positioning a right and a left breast of the subject; (2) providing two x-ray sources, a right and a left positioned to image the right breast and the left breast, respectively; (3) positioning an x-ray detector between the right and left breasts configured to allow an x-ray beam generated by the right or the left x-ray source to pass through the right or the left breast of the subject and to project onto a detecting surface of the x-ray detector, to register one or more images of the right or the left breast; (4) positioning the x-ray detector relative to the right or left breast to allow the registration of one or more images thereof; (5) imaging the right or the left breast to register one or more images on the x-ray detector; (6) positioning the x-ray detector relative to the left or right breast to allow the registration of one or more images thereof; and (7) imaging the left or the right breast to register one or more images on the x-ray detector.

In yet another aspect, the invention generally relates to a method for generating x-ray images of breasts of a subject. The method includes: (1) providing a support for positioning a right and a left breast of the subject; (2) providing an assembly of an array of one or more x-ray sources and an x-ray detector positioned on opposite sides of a breast of the subject to be imaged and configured to allow an x-ray beam generated by the array or one or more x-ray sources to pass through a breast of the subject and to project onto a detecting surface of the x-ray detector; (3) positioning the assembly of the array of one or more x-ray sources and the x-ray detector relative to one breast to allow the registration of one or more images thereof; (4) imaging the breast to register one or more images on the x-ray detector; (5) positioning the assembly of the array of one or more x-ray sources and the x-ray detector relative to the other breast to allow registration of one or more images of the other breast; and (6) imaging the other breast to register one or more images on the x-ray detector.

DETAILED DESCRIPTION OF THE INVENTION

The present invention provides unique x-ray breast imaging systems and related methods that are applicable to contrast enhanced digital mammography and contrast enhanced digital breast tomosynthesis. The invention enables fast, cost-effective and accurate x-ray imaging.

A unique aspect of the invention is the use of a single x-ray detector with the versatility of working in association with diverse x-ray source set-ups (e.g., one or two x-ray sources or arrays of x-ray sources) to generate fast and high-quality images, all without the need to reposition the patient during the imaging procedure. The invention is directly applicable to contrast enhanced digital mammography and contrast enhanced tomographic imaging such as digital breast tomosynthesis, which are considered as highly-promising candidates for clinical success. Moreover, the invention addresses limitations of existing systems and enables simultaneous acquisition of images for bilateral exams. Another exemplary feature of the present invention addresses the limitations of existing systems by energizing the x-ray sources and synchronizing the x-ray detector readout with the corresponding x-ray source at a high frame-rate (e.g., up to 30 frames/second, corresponding to a temporal resolution of 33 milliseconds).

System and Apparatus

The invention features novel systems for making bilateral radiographic and tomographic images of the breast without the need for repositioning the patient. In a preferred embodiment of the invention, a system according to the invention includes (1) either a patient support table or a patient protective barrier with a single large opening or two smaller openings through which the breasts extend to the x-ray field of view for imaging, (2) one or a plurality of x-ray sources, and (3) a single x-ray detector.

The x-ray sensitive surface of the detector may have pixel pitch in the range of about 0.03 mm to 0.5 mm, and signal from adjacent pixels can be combined by symmetric or asymmetric grouping of adjacent pixels (pixel binning). An x-ray controller is configured to control the operation of the x-ray source and to synchronize with the readout of the x-ray detector assembly to provide images at a high temporal rate in the range of from about 0.1 to about 30 frames/second or at single images every few seconds. The approach also allows for alternating acquisition of images between the right and left breasts. A computational unit configured to perform mathematical operation to provide radiographic images and tomographic images of imaged breasts. Additionally, bilateral breast stabilization, if needed, can be achieved to minimize artifacts due to patient motion using mild compression such that blood flow to the breast is not impeded.

Exemplary Embodiment No. 1

Figure 1:
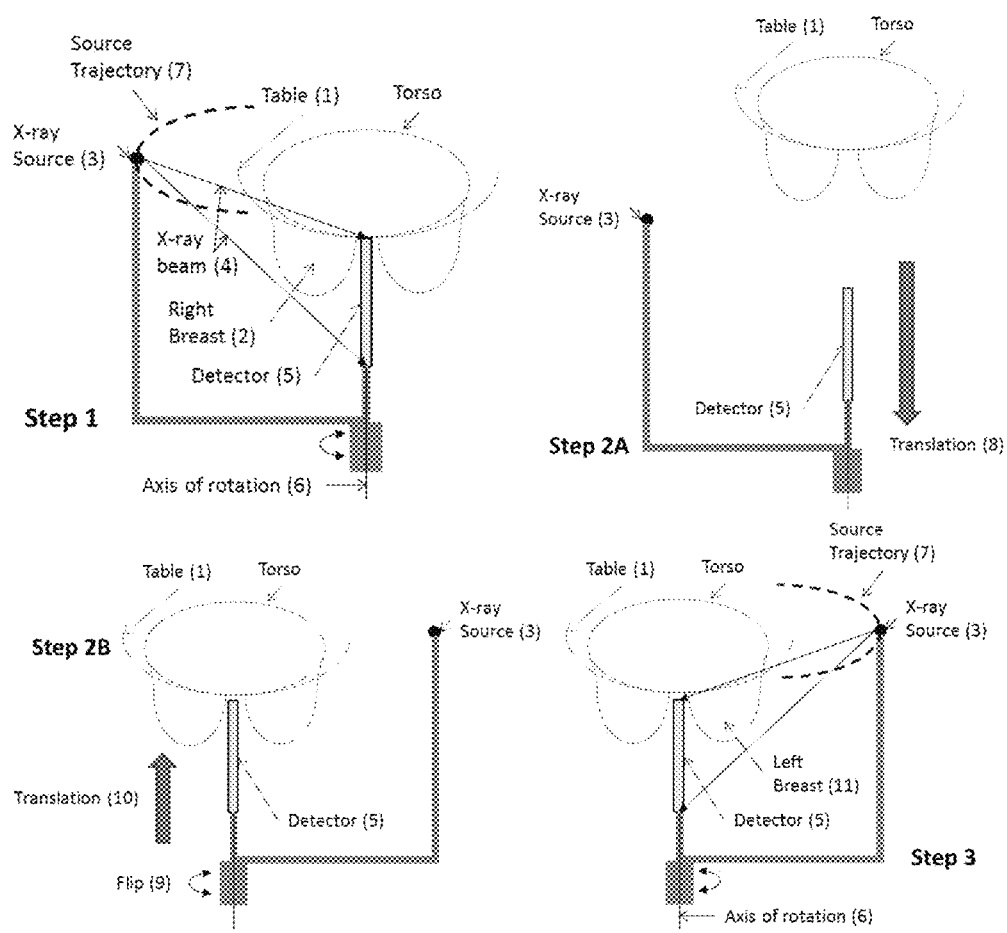
FIG. 1 schematically illustrates an exemplary embodiment of the invention, wherein the axis of rotation is aligned with the x-ray detector that is positioned between the two breasts, and wherein one breast is imaged first, followed by translation of the x-ray source and x-ray detector assembly away from the patient, flipping of the x-ray source and x-ray detector assembly, and translation of the x-ray source and x-ray detector assembly, when the system is ready to image the other breast.

FIG. 1 schematically depicts an exemplary system according to the present invention. The system images one breast at a time without the need to reposition the patient, thus allowing fast acquisition of bilateral breast images. The order of imaging can be interchanged between the left and right breasts. As an example, the right breast of patient is imaged first, followed by translation of the x-ray source and x-ray detector assembly away from the patient, flipping of the x-ray source and x-ray detector assembly, and translation of the x-ray source and x-ray detector assembly, when the system is ready to image the left breast. Alternatively, one or more images are acquired on one breast, the system is repositioned to the other breast for acquisition of one or more images and the system return to the other breast for acquisition of additional images.

Referring to FIG. 1 (top left), which schematically illustrates Step 1 of this exemplary embodiment, the patient is supported on a support table 1 with the breasts pendant through the openings in the table. The axis of rotation 6 is aligned with the x-ray detector 5 that is positioned between the two breasts. The right breast of the patient is imaged as in Step 1, where the x-ray source 3 produces the x-ray beam 4 that irradiates the right breast 2. The transmitted x-ray beam is detected by the x-ray detector 5.

For radiographic or mammographic imaging (with or without x-ray contrast agent administered to the patient), the x-ray source and x-ray detector remain stationary. For tomographic imaging (with or without x-ray contrast agent administered to the patient), the x-ray source alone is moved along the source trajectory 7.

After imaging the right breast, the x-ray source is turned off and the x-ray detector assembly is repositioned for the left breast as shown in Step 2, FIG. 1 (top right and bottom left), wherein the x-ray source and x-ray detector assembly is first translated away from the patient (represented by block arrow, Translation 8, Step 2A). Then, the x-ray source and x-ray detector assembly is flipped (represented by the double arrowed curve, Flip 9, Step 2B), and translated towards the patient (represented by the block arrow, Translation 10, Step 2B). The left breast 11 is imaged by the x-ray detector 5 with the x-ray source 3 (Step 3). As mentioned, the order of imaging the left and right breasts can be interchanged.

In another exemplary configuration, the entire apparatus can be made into an upright system by replacing the patient support table with a patient protective barrier.

In an exemplary variant of this embodiment for tomographic imaging, the x-ray source is coupled to the detector and move in synchrony centered at the axis of rotation. This maintains the relative orientation between the x-ray sensitive surface of the x-ray detector assembly and the x-ray beam. Advantages for maintaining the relative orientation between the x-ray detector and x-ray tube include: (a) avoiding image quality degradation due to oblique x-ray incidence when the rotation angle is varied, and (b) allowing the use of x-ray anti-scatter grids in front of the x-ray sensitive surface that is focused to the x-ray source.

In another exemplary variant of this embodiment for tomographic imaging, the angular movement of the x-ray detector is fixed as a ratio of the x-ray source movement. As an example, for every 3-degrees of angular movement of the x-ray source, the x-ray detector moves by 1-degree. This allows for a larger angular range of x-ray source movement.

In another exemplary variant of this embodiment for tomographic imaging, the x-ray detector is stationary, while the x-ray source moves along a pre-determined trajectory. Advantage of this variant includes that no additional mechanical clearance would be needed for detector movement.

Exemplary Embodiment No. 2

Figure 2:
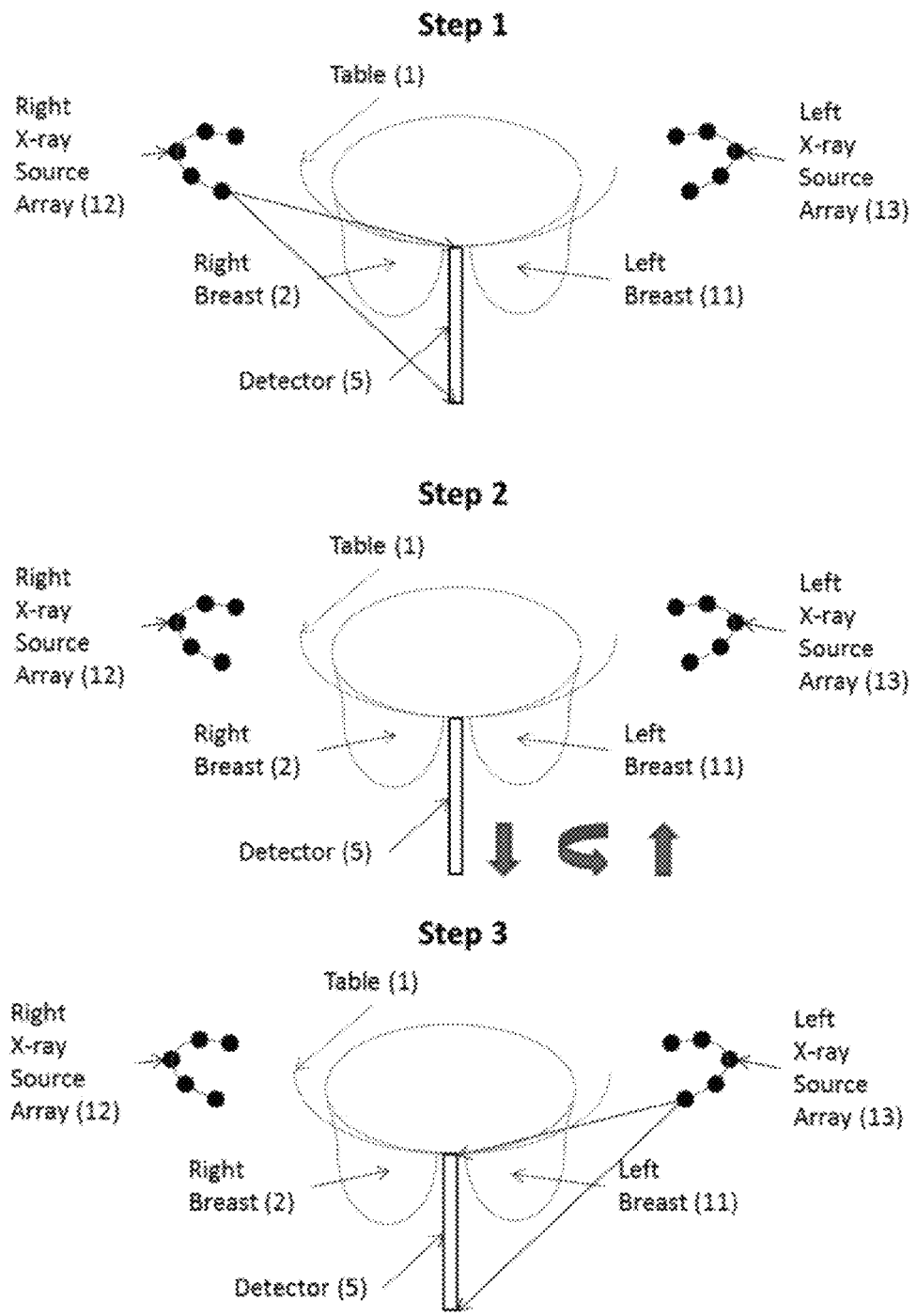
FIG. 2 schematically illustrates an exemplary embodiment of the invention, wherein the system has two arrays of x-ray sources, one array each for imaging the left and the right breasts, and wherein the x-ray detector can be repositioned to image the left or right breast.

As schematically illustrated in FIG. 2, the system is similar to that FIG. 1 and the patient is supported on a support table 1 with the breasts pendant through the openings in the table. In FIG. 2, the system has two arrays of x-ray sources (12 and 13), one array each for imaging the left and the right breasts. The x-ray source array may take any suitable configuration, e.g., linear, curved, curvilinear, rectangular or square. The system utilizes a single x-ray detector 5, which can be quickly repositioned to image the left or right breast by translating the x-ray detector away from the patient, flipping it, and translating it towards the patient. Flipping can be either horizontal or vertical such that the x-ray sensitive surface of the x-ray detector faces the incident x-ray beam.

An advantage of this embodiment is that no movement of the x-ray source is needed, which improves the mechanical accuracy for positioning. Similar to the variants described in Exemplary Embodiment No. 1 above, the x-ray detector can be stationary or can be angularly displaced to track the individual x-ray source of the x-ray source array or can be angularly displaced by a fixed ratio with respect to the individual x-ray source of the x-ray source array.

Referring to FIG. 2 (top, Step 1) for tomographic imaging of the right breast 2, each x-ray source within the right x-ray source array 12 is energized. The x-ray beam transmits through the right breast 2 and is imaged by the x-ray detector 5. Then, the x-ray detector is translated away from the patient, flipped and translated back towards the patient (represented by the block arrows, Step 2). Similar to Step 1, the left breast 11 is imaged by the left x-ray source array 13 and the x-ray detector 5. Again, the order of imaging of the left and right breasts can be switched.

In another exemplary configuration of this embodiment, the entire apparatus can be fabricated as an upright system, wherein table 1 is replaced by a protective barrier so that the patient does not come into contact with the moving parts of the apparatus.

In another exemplary variant, one of the individual x-ray sources of each x-ray source array depicted in FIG. 2 is replaced by a high-powered x-ray source (e.g., a conventional rotating anode x-ray tube) to provide higher power and x-ray fluence.

Exemplary Embodiment No. 3

Figure 3:
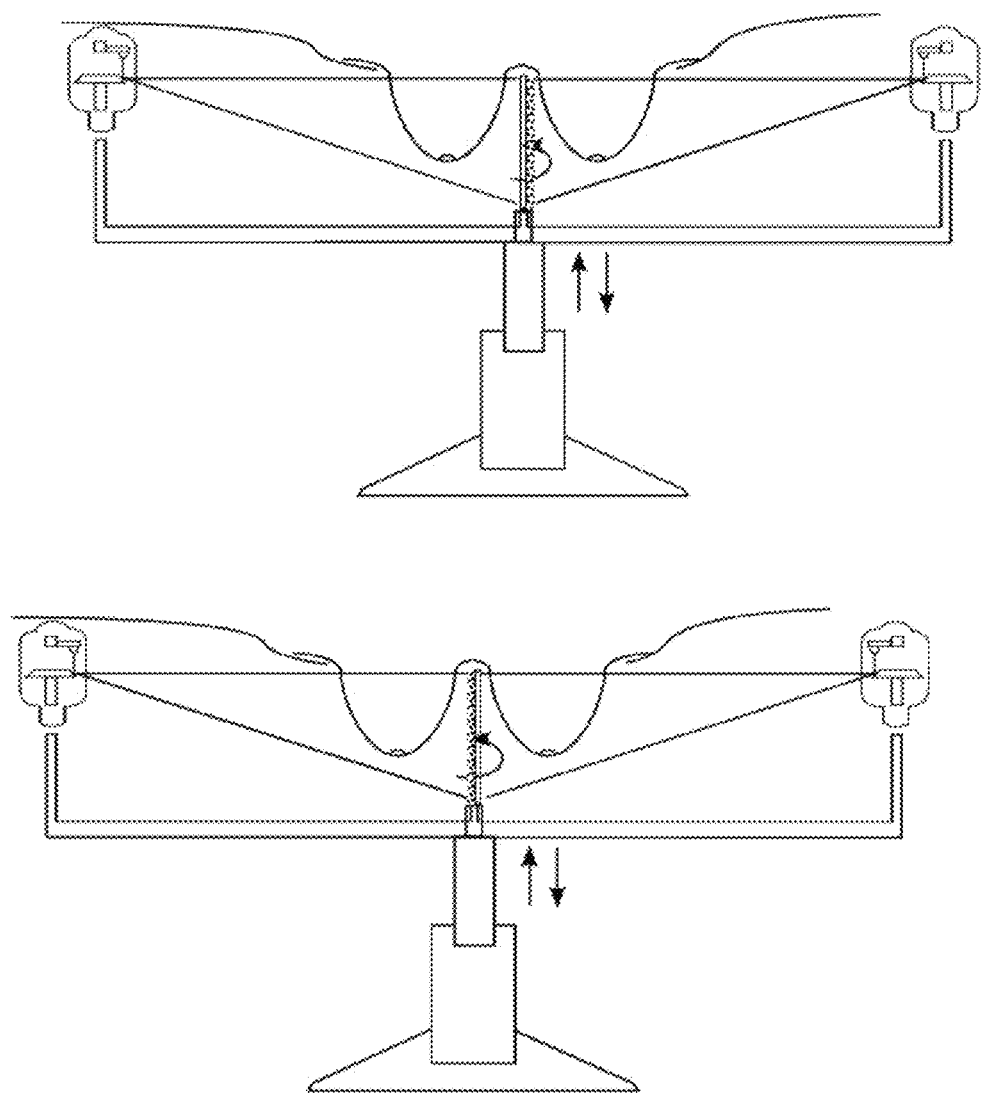
FIG. 3 schematically illustrates an exemplary embodiment of the invention, wherein the system includes two x-ray sources, one each for imaging the left and right breasts, and wherein translation between the two breasts can be achieved by translating the x-ray source and x-ray detector assembly and by flipping the detector assembly for the x-ray sensitive part to face the x-ray source.

Referring to FIG. 3, the schematically depicted system includes two x-ray sources, one each for imaging the left and right breasts. The patient is supported on table 1 with the breasts pendant through the openings in support table 1. The axis of rotation 6 (represented by the curved arrow) is located between the two breasts (2 and 11). A single x-ray detector 5 is used.

Referring to FIG. 3 (top), the right breast 2 is imaged with the right x-ray source 14. After imaging the right breast, the x-ray detector 5 is translated away from the patient (represented by the opposite arrows), flipped, and translated back into position to facilitate imaging of the left breast 11, as illustrated in FIG. 3 (bottom). The left x-ray source 15 is then activated for imaging the left breast 11.

Exemplary variants of this embodiment for tomographic imaging include angular movement of the x-ray detector assembly in synchrony with the x-ray tube angular movement, or a stationary x-ray detector, or an x-ray detector that rotates at a fixed ratio with respect to x-ray source angular movement, similar to that described in connection with Exemplary Embodiment No. 1 above.

In another exemplary configuration of this embodiment, the entire apparatus can be fabricated as an upright system, wherein table 1 is replaced by a protective barrier so that the patient does not come into contact with the moving parts of the apparatus. In this configuration the patient will be in the standing or seating position instead of the prone position on a table.

Exemplary Embodiment No. 4

Figure 4:
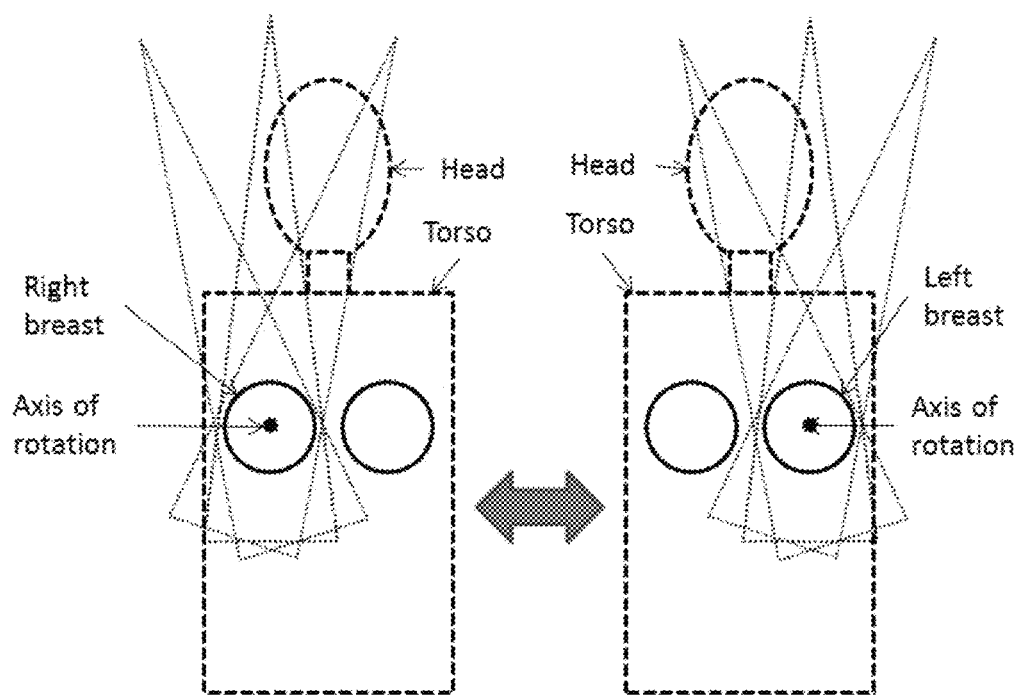
FIG. 4 schematically illustrates an exemplary embodiment of the invention, wherein the axis of rotation for the x-ray source and x-ray detector assembly is centered near the middle of the breast being imaged, and wherein translation between the two breasts can be achieved by translating the x-ray source and x-ray detector assembly or by translating the patient support table.

FIG. 4 schematically depicts a system wherein the axis of rotation for the x-ray source and x-ray detector assembly is within one of the two breasts for imaging that breast.

Referring to FIG. 4 (left), the right breast 2 is first imaged. Upon completion of imaging the right breast, the x-ray source 15 and x-ray detector 5 assembly is translated so that the axis of rotation 6 is centered about the middle of the left breast 11, as illustrated in FIG. 4 (right). The translation (represented by bi-directional block arrow) between the two breasts can be achieved by translating the x-ray source and x-ray detector assembly or by translating the patient support table. Moving the x-ray source and x-ray detector assembly may be preferred for an upright system. Translating the patient support table may be suitable for a prone imaging system.

Exemplary variants of this embodiment include replacing the x-ray source with an array of x-ray sources with or without a high-powered x-ray source similar to that described above. Additional exemplary variants for tomographic imaging include a stationary x-ray detector or one that rotates at a fixed ratio with respect to x-ray source angular movement, similar to that described in Exemplary Embodiment No. 1.

In another exemplary configuration of this embodiment, the entire apparatus can be fabricated as an upright system, wherein table 1 is replaced by a protective barrier so that the patient does not come into contact with the moving parts of the apparatus.

Exemplary Embodiment No. 5

Figure 5:
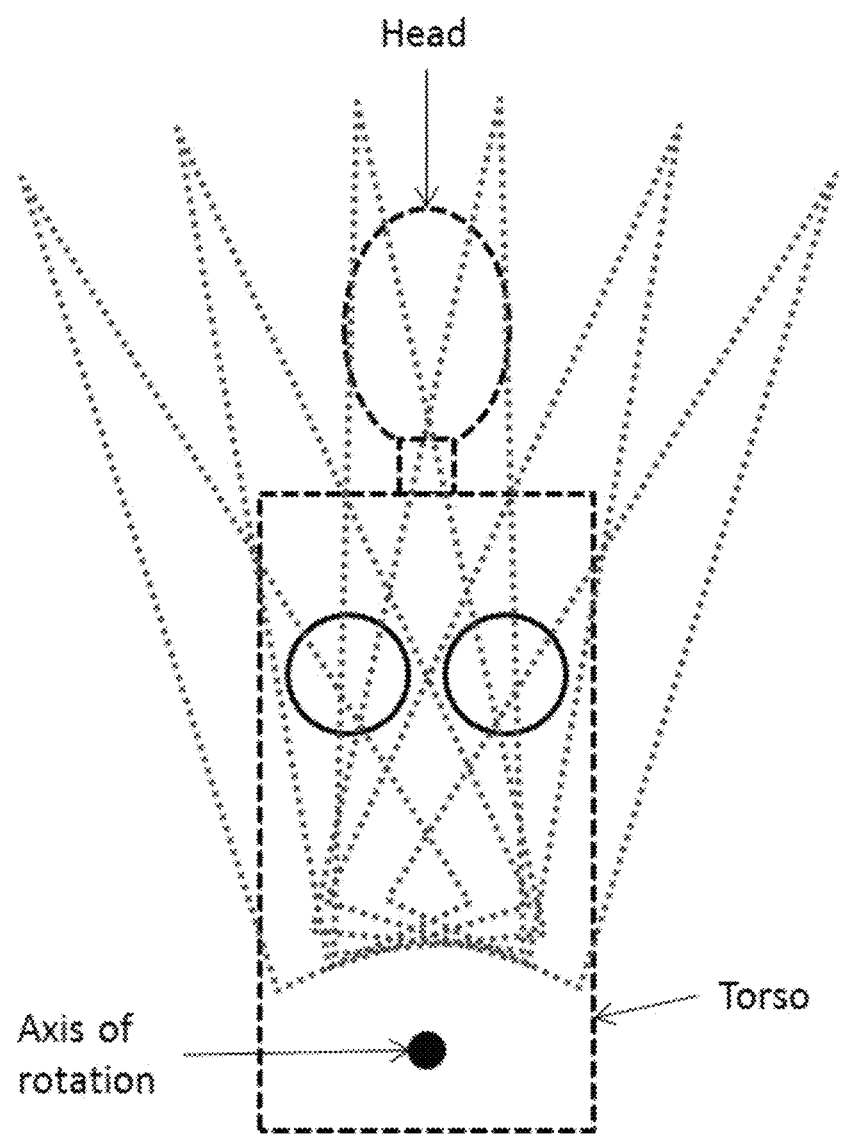
FIG. 5 schematically illustrates an exemplary embodiment of the invention, wherein the axis of rotation for the x-ray source and x-ray detector assembly is below the breasts in the vertical direction and is located horizontally between the two breasts, and wherein the x-ray source and x-ray detector assembly move in synchrony and cover both breasts.

In the exemplary system depicted in FIG. 5, the axis of rotation 6 for the x-ray source and x-ray detector assembly is below the breasts in the vertical (superior-inferior) direction and is located horizontally (left-right). The x-ray source and x-ray detector assembly move in synchrony and cover both breasts.

Exemplary variants of this embodiment include replacing the x-ray source with an array of x-ray sources with or without a high-powered x-ray source similar to that described herein above.

In another exemplary configuration of this embodiment, the entire apparatus can be fabricated as an upright system, wherein table 1 is replaced by a protective barrier so that the patient does not come into contact with the moving parts of the apparatus.

Exemplary Embodiment No. 6

Figure 6:
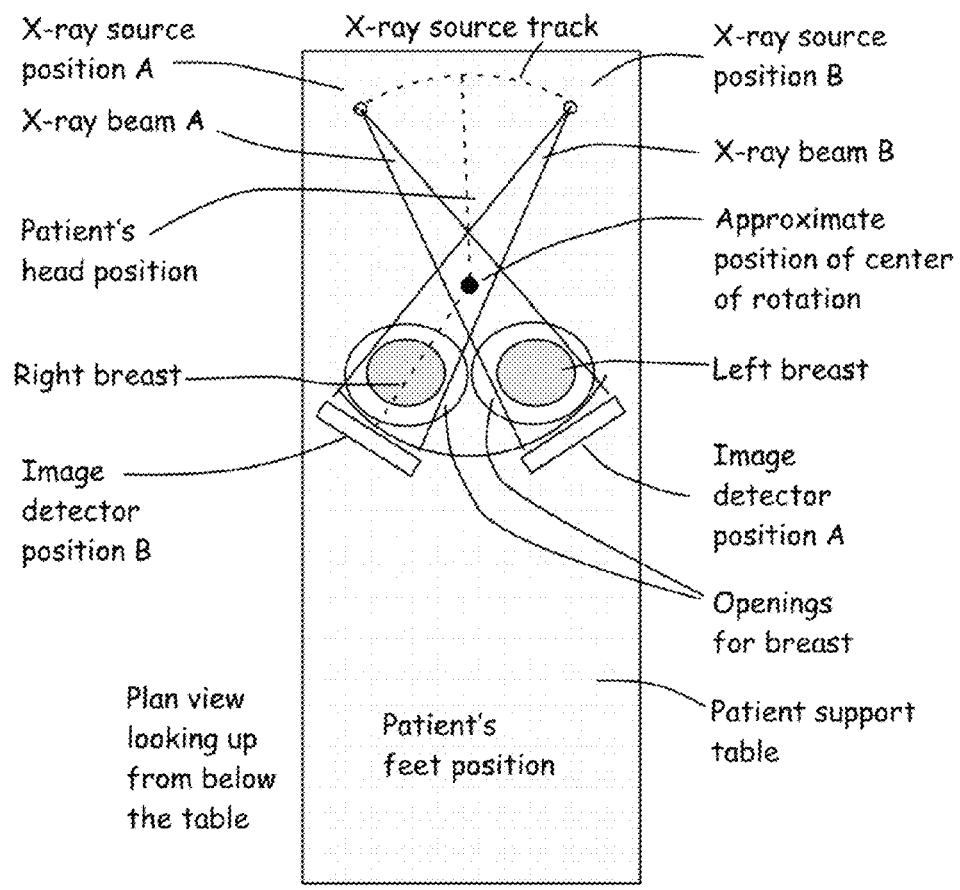
FIG. 6 schematically illustrates an exemplary embodiment of the invention, wherein the axis of rotation for the x-ray source and x-ray detector assembly is found above the breasts in the vertical direction and is located horizontally between the two breasts, and wherein the x-ray source and x-ray detector assembly move in synchrony and cover both breasts.

Referring to FIG. 6, the schematically depicted system has the axis of rotation 6 for the x-ray source and x-ray detector assembly above the breasts in the vertical (superior-inferior) direction and is located horizontally (left-right) between the two breasts (2 and 11). The patient is supported on a table 1 with the breasts pendant through the openings in the table. The x-ray source 16 and x-ray detector 5 assembly move in synchrony and cover both breasts.

In another exemplary configuration of this embodiment, the entire apparatus can be fabricated as an upright system, wherein table 1 is replaced by a protective barrier so that the patient does not come into contact with the moving parts of the apparatus.

Exemplary variants of this embodiment include replacing the x-ray source with an array of x-ray sources with or without a high-powered x-ray source similar to that described herein above.

Exemplary Embodiment No. 7

Figure 7:
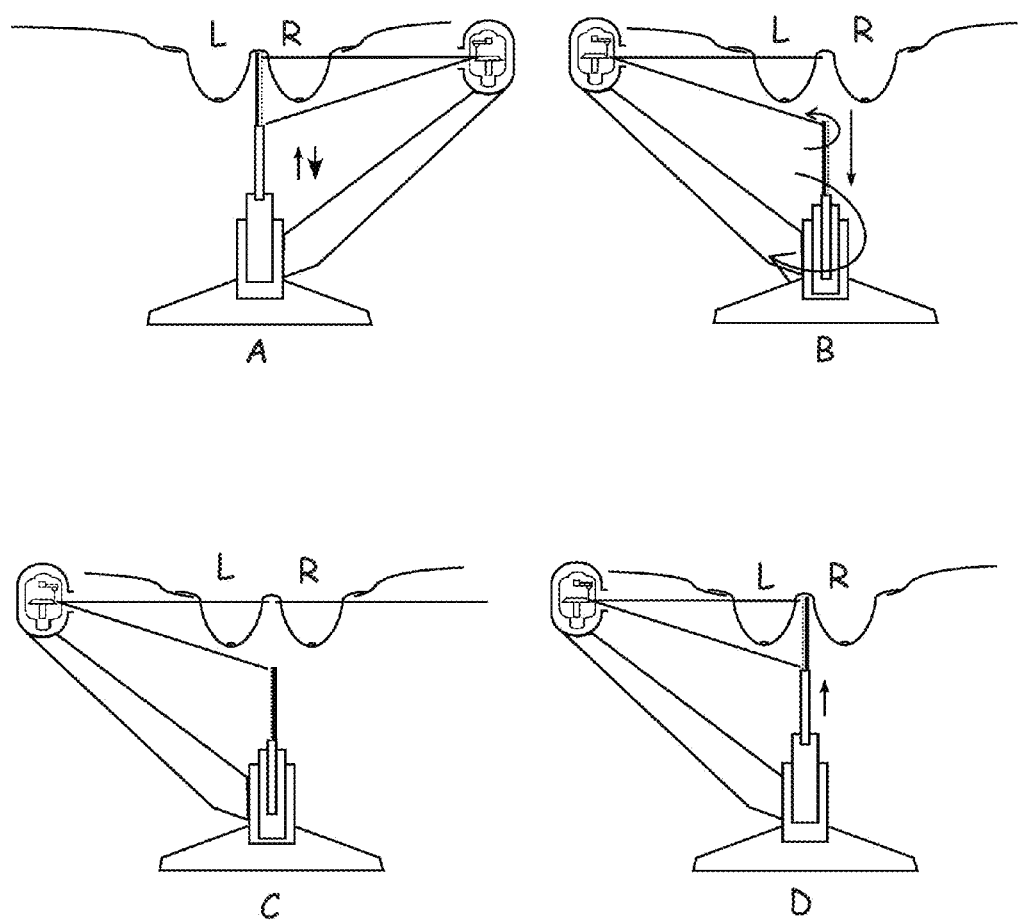
FIG. 7 schematically illustrates an exemplary embodiment of the invention, wherein the system includes an x-ray source and translation between the two breasts can be achieved by independently relocating the x-ray source and rotating/translating x-ray detector.

Referring to FIG. 7A, an x-ray source or array of x-ray sources irradiates the right breast and a single or multiple images are acquired at a fixed position or at an arc typically less than +/−90 degrees from this position. Vertical arrows show that the detector can be moved in the vertical direction for the next step. FIG. 7B, the x-ray source or array of sources is moved to the next position to irradiate the left breast for a series of image acquisitions. As the x-ray source or array of sources is moved to this position typically by a 180-degree rotation, the detector is moved vertically to clear the breast and then rotated 180 degrees to face the x-ray source. In FIG. 7C, the x-ray source or array of sources are in the proper orientation but the detector is moved vertically to position between the left and right breast. FIG. 7D shows that the x-ray source or array of sources is in the proper position for the next image series acquisition. Noted here is that the position of the x-ray sources or array of sources for imaging the right and left breast does not have to be exactly 180 degrees apart as illustrated as an exemplary embodiment.

Methods and Applications

The present invention also features novel methods for obtaining bilateral radiographic and tomographic images of the breast with high-temporal and high-spatial resolution to observe contrast-enhancement kinetics using, for example, the systems disclosed herein. The patient is positioned such that the breasts are in the field of view for x-ray imaging. Stabilization of the breasts can be achieved by mild compression (e.g., about 5 decaNewtons).

Contrast Enhanced Digital Mammography

For contrast enhanced digital mammography, at least one radiographic image is acquired before injection of contrast media (the "mask image"). In a preferred embodiment depending on the contrast media used, the applied peak kilovoltage (kVp) of the x-ray source is selected to be at or above the k-absorption edge of the contrast media for image acquisition. For example, when iodinated contrast media is used, the applied peak voltage is in the range of about 35 kVp to about 100 kVp for acquiring the radiographic images.

Figure 8:
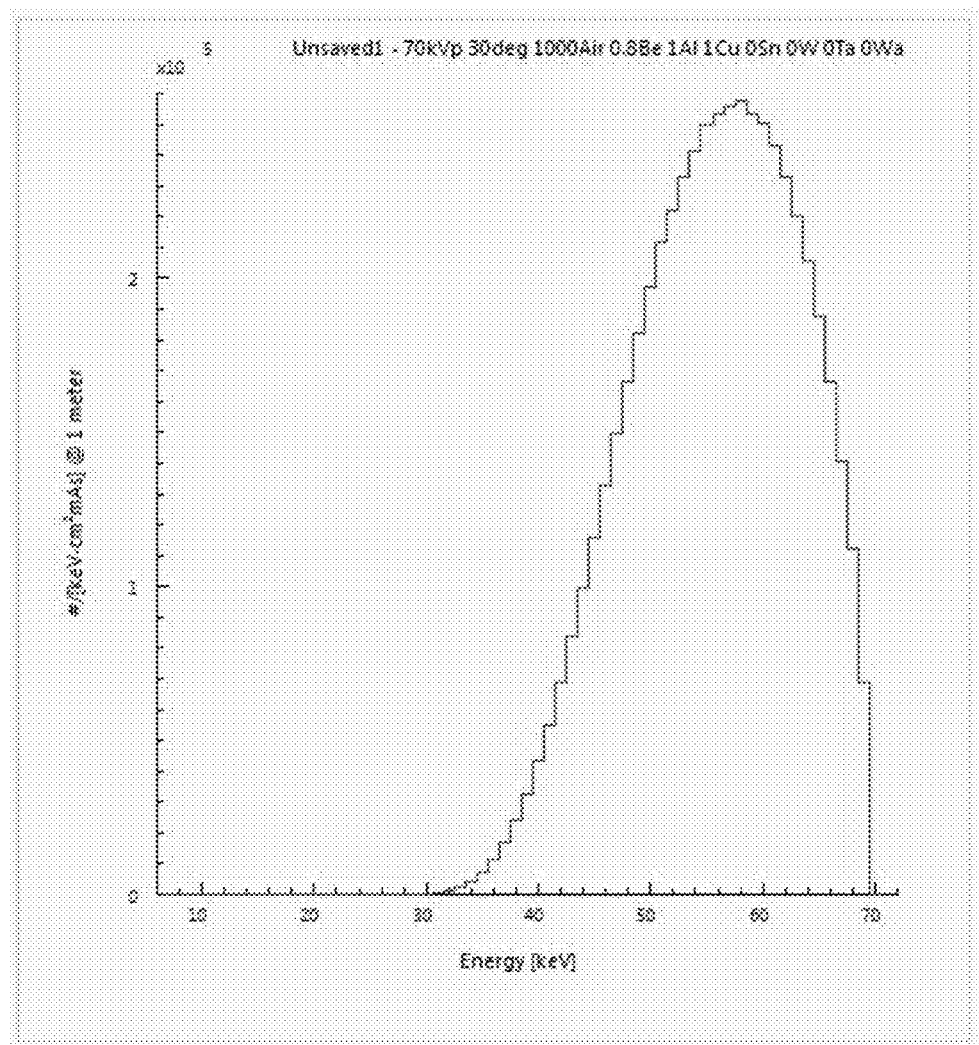
FIG. 8 shows an exemplary x-ray spectrum for contrast enhanced imaging with iodinated contrast media (k-edge of iodine, 33.2 keV).

An exemplary x-ray spectrum for contrast enhanced imaging with iodinated contrast media (k-edge of iodine is 33.2 keV) is shown in FIG. 8, where a 70 kVp tungsten anode x-ray spectrum is filtered by 1 mm of copper and 1 mm of Aluminum filtration in addition to the inherent x-ray tube filtration of 0.8 mm of beryllium, which can be used for contrast enhanced digital mammography or contrast enhanced digital breast tomosynthesis using iodinated contrast media. (Poludniowski, et al. 2009 *Physics in Medicine and Biology* 54 (19), N433-438; Poludniowski 2007 *Medical Physics* 34 (6), 2175-2186; Poludniowski et al. 2007 *Medical Physics* 34 (6), 2164-2174.) Most x-ray spectrum is above the k-edge of iodine and hence would be suitable.

Additionally, inhaled non-radioactive stable Xenon gas (k-edge of Xe is 34.5 keV) or injected gold nanoparticles (k-edge of gold is 80.7 keV) or any other appropriate x-ray contrast media can be used as an alternative to iodinated contrast media. A bolus of contrast media is either injected or inhaled. A temporal sequence of at least two images is acquired after administration of contrast media using the same kVp and x-ray beam quality as the "mask image". The temporal enhancement pattern is determined on a pixel-by-pixel basis by weighted logarithmic subtraction of the radiographic images acquired after contrast administration from the "mask image" obtained before contrast administration. The determined temporal enhancement pattern can be color-coded to represent the intensity of contrast enhancement and is superimposed on the "mask image" that provides anatomic features through image fusion techniques. The combined display of anatomic features and contrast enhancement kinetics allow for localized analysis of regions that are considered as abnormal.

Analysis of contrast enhancement kinetics may include: the time between arterial enhancement and enhancement of abnormality; the spatial pattern of enhancement of abnormality (e.g., centrifugal or centripetal enhancement); the duration, the rate of enhancement, and the rate constant of enhancement of the abnormality that represent the "wash-in" characteristics; the duration, the rate constant and the rate at which the contrast media within the enhanced abnormality is dissipated that represent the "wash-out" characteristics; and temporal frequency analysis through Fourier transform.

Additionally, the analysis can be compared between the two breasts so that improved determination of abnormal regions can be achieved for detection and diagnosis of breast cancer.

Contrast Enhanced Digital Tomosynthesis

For contrast enhanced digital breast tomosynthesis, at least one tomographic image is acquired before injection of contrast media and is referred to as the "mask tomogram". In a preferred embodiment and depending on the contrast media used, the applied peak kilovoltage of the x-ray source is selected to be at or above the k-absorption edge of the main absorbing element in the contrast media for image acquisition. Then, a bolus of contrast media is either injected or inhaled.

A temporal sequence of at least two tomographic images is acquired after administration of contrast media using the same kVp and x-ray beam quality as the "mask tomogram". The temporal enhancement pattern is determined on a voxel-by-voxel basis by weighted subtraction of the tomographic images acquired after contrast administration from the "mask tomogram" obtained before contrast administration. The determined temporal enhancement pattern can be color-coded to represent the intensity of contrast enhancement and is superimposed on the "mask tomogram" that provides anatomic features through image fusion techniques. The combined display of anatomic features and contrast enhancement kinetics allow for localized analysis of regions that are considered as abnormal.

Analysis of contrast enhancement kinetics may include the time between arterial enhancement and enhancement of abnormality; the spatial pattern of enhancement of abnormality (e.g., centrifugal or centripetal enhancement); the duration, the rate of enhancement, and the rate constant of enhancement of the abnormality that represent the "wash-in" characteristics; the duration, the rate constant and the rate at which the contrast media within the enhanced abnormality is dissipated that represent the "wash-out" characteristics; and temporal frequency analysis through Fourier transform. Additionally, the analysis can be compared between the two breasts so that improved determination of abnormal regions can be achieved for detection and diagnosis of breast cancer.

Thus, the invention described herein is directly applicable to contrast enhanced digital mammography and contrast enhanced digital breast tomosynthesis, which are considered as highly-promising candidates for clinical success.

In one aspect, the invention generally relates to a system for generating x-ray images of breasts of a subject. The system includes: (1) a support for positioning a right and a left breast of the subject; (2) an assembly of an x-ray source and an x-ray detector; (3) a controller unit coupled to and command the operation of the x-ray source and the x-ray detector assembly; and (4) a computation unit configured to receive, analyze, display and/or store the one or more images of the right or the left breast. The x-ray source and the x-ray detector are configured to allow an x-ray beam generated by the x-ray source to pass through the right or the left breast of the subject and to project onto a detecting surface of the x-ray detector, positioned between the right and left breasts, to register one or more images of the right or the left breast; and wherein the assembly of the x-ray source and the x-ray detector is rotatable in synchrony around an axis located between the right and left breasts and normal to the subject's chest, and is translatable in one or more dimensions relative to the subject's chest. The assembly of the x-ray source and the x-ray detector is first positioned relative to one breast to allow the registration of one or more images thereof and is then positioned relative to the other breast to allow registration of one or more images of the other breast.

In certain preferred embodiments, the x-ray source and the x-ray detector remain stationary when taking the one or more images of the right breast and remain stationary when taking the one or more images of the left breast.

In certain preferred embodiments, the x-ray detector remains stationary and the x-ray source travels along a pre-defined trajectory when taking the one or more images of the right breast and the x-ray detector remains stationary and the x-ray source travels along a pre-defined trajectory when taking the one or more images of the left breast.

In certain preferred embodiments, the assembly of the x-ray source and the x-ray detector is rotatable in synchrony around an axis located substantially mid-way (centered) between the right and left breasts and normal to the subject's chest.

In certain embodiments, the assembly of the x-ray source and the x-ray detector is moveable longitudinally along an axis to and from the subject's chest, is translatable along an axis to and from the subject's head, or a combination thereof.

In certain preferred embodiments, the system is useful for radiographic or mammographic imaging without x-ray contrast agent administered to the subject prior to imaging.

In certain preferred embodiments, the system is useful for radiographic or mammographic imaging with x-ray contrast agent administered to the subject prior to imaging.

In certain preferred embodiments, the system is useful for tomographic imaging with x-ray contrast agent administered to the patient prior to imaging. In certain preferred embodiments, the system is useful for tomographic imaging without x-ray contrast agent administered to the patient prior to imaging.

In certain preferred embodiments, the system is configured to allow imaging of the subject to take place while the subject is in a prone posture.

In certain preferred embodiments, the system is configured to allow imaging of the subject to take place while the subject is in an upright posture.

In some embodiments, the x-ray detector remain stationary and the x-ray source travels along a pre-defined trajectory when taking the one or more images of the right breast and remain stationary when taking the one or more images of the left breast.

In another aspect, the invention generally relates to a system for generating x-ray images of breasts of a subject. The system includes: (1) a support for positioning a right and a left breast of the subject; (2) two arrays of x-ray sources, a right array and a left array positioned to image the right breast and the left breast, respectively, wherein the x-ray sources of each of the two arrays are arranged along a pre-defined trajectory; (3) an x-ray detector, positioned between the right and left breasts, configured to allow an x-ray beam generated by the right or the left array of x-ray sources to pass through the right or the left breast of the subject and to project onto a detecting surface of the x-ray detector to register one or more images of the right or the left breast; (4) a controller unit coupled to and command the operation of the x-ray detector; and (5) a computation unit configured to receive, analyze, display and/or store the one or more images of the right or the left breast. The x-ray detector is rotatable around an axis located between the right and left breasts and normal to the subject's chest, and is translatable in one or more dimensions relative to the subject's chest. The x-ray detector is first positioned relative to one breast to allow the registration of one or more images thereof and is then positioned relative to the other breast to allow registration of one or more images of the other breast.

In some embodiments, the two arrays of x-ray sources remain stationary during imaging. In some embodiments, the x-ray detector is angularly displaced such that it tracks the individual x-ray source of the x-ray source array.

In yet another aspect, the invention generally relates to a system for generating x-ray images of breasts of a subject. The system includes: (1) a support for positioning a right and a left breast of the subject; (2) two x-ray sources, a right and a left positioned to image the right breast and the left breast, respectively; (3) an x-ray detector, positioned between the right and left breasts, configured to allow an x-ray beam generated by the right or the left array of x-ray sources to pass through the right or the left breast of the subject and to project onto a detecting surface of the x-ray detector to register one or more images of the right or the left breast; (4) a controller unit coupled to and command the operation of the x-ray detector; and (5) a computation unit configured to receive, analyze, display and/or store the one or more images of the right or the left breast. The x-ray detector is rotatable around an axis located between the right and left breasts and normal to the subject's chest, and is translatable in one or more dimensions relative to the subject's chest. The x-ray detector is first positioned relative to one breast to allow the registration of one or more images thereof and is then positioned relative to the other breast to allow registration of one or more images of the other breast.

In yet another aspect, the invention generally relates to a system for generating x-ray images of breasts of a subject. The system includes: (1) a support for positioning a right and a left breast of the subject; (2) an assembly of an x-ray source and an x-ray detector positioned on opposite sides of a breast of the subject to be imaged and configured to allow an x-ray beam generated by the x-ray source to pass through a breast of the subject and to project onto a detecting surface of the x-ray detector; (3) a controller unit coupled to and command the operation of the assembly of an x-ray source and an x-ray detector; and (4) a computation unit configured to receive, analyze, display and/or store the one or more images of the right or the left breast. The assembly of the x-ray source and the x-ray detector is rotatable around an axis located within the breast being imaged and normal to the subject's chest, and is translationally moveable along the said axis. The assembly of the x-ray source and the x-ray detector is first positioned relative to one breast of the subject to allow the registration of one or more images thereof and is then positioned relative to the other breast of the subject to allow registration of one or more images thereof.

In yet another aspect, the invention generally relates to a system for generating x-ray images of breasts of a subject. The system includes: (1) a support for positioning a right and a left breast of the subject; (2) an assembly of an x-ray source and an x-ray detector positioned on opposite sides of a breast of the subject to be imaged and configured to allow an x-ray beam generated by the x-ray source to pass through the breast of the subject and to project onto a detecting surface of the x-ray detector; (3) a controller unit coupled to and command the operation of the assembly; and (4) a computation unit configured to receive, analyze, display and/or store the one or more images of the right or the left breast. The assembly of the x-ray source and the x-ray detector is rotatable around an axis located between and below the breasts and normal to the subject's chest; The assembly of the x-ray source and the x-ray detector is first positioned relative to one breast of the subject to allow the registration of one or more images thereof and is then positioned relative to the other breast of the subject to allow registration of one or more images thereof.

In yet another aspect, the invention generally relates to a system for generating x-ray images of breasts of a subject. The system includes: (1) a support for positioning a right and a left breast of the subject; (2) an assembly of an x-ray source and an x-ray detector positioned on opposite sides of a breast of the subject to be imaged and configured to allow an x-ray beam generated by the x-ray source to pass through the breast of the subject and to project onto a detecting surface of the x-ray detector; (3) a controller unit coupled to and command the operation of the assembly; and (4) a computation unit configured to receive, analyze, display and/or store the one or more images of the right or the left breast. The assembly of the x-ray source and the x-ray detector is rotatable around an axis located between and above the subject's breasts and normal to the subject's chest. The assembly of the x-ray source and the x-ray detector is first positioned relative to one breast of the subject to allow the registration of one or more images thereof and is then positioned relative to the other breast of the subject to allow registration of one or more images thereof.

The present invention also generally relates to methods for x-ray images using a system disclosed herein.

In yet another aspect, the invention generally relates to a method for generating x-ray images of breasts of a subject. The method includes: (1) providing a support for positioning a right and a left breast of the subject; (2) providing an assembly of an x-ray source and an x-ray detector; (3) positioning the assembly of the x-ray source and the x-ray detector relative to one breast to allow the registration of one or more images thereof; (4) imaging the breast to register one or more images on the x-ray detector; (5) positioning the assembly of the x-ray source and the x-ray detector relative to the other breast to allow registration of one or more images of the other breast; and (6) imaging the other breast to register one or more images on the x-ray detector. The x-ray source and the x-ray detector are configured to allow an x-ray beam generated by the x-ray source to pass through the right or the left breast of the subject and to project onto a detecting surface of the x-ray detector, positioned between the right and left breasts, to register one or more images of the right or the left breast. The assembly of the x-ray source and the x-ray detector is rotatable in synchrony around an axis located between the right and left breasts and normal to the subject's chest, and is longitudinally moveable along the axis to and from the subject's chest In some embodiments, the x-ray source and the x-ray detector remain stationary when taking the one or more images of the right breast and remain stationary when taking the one or more images of the left breast.

In some embodiments, the x-ray detector remain stationary and the x-ray source travels along a pre-defined trajectory when taking the one or more images of the right breast and remain stationary when taking the one or more images of the right breast.

In some embodiments, the method further includes administering x-ray contrast agent to the subject prior to imaging.

In yet another aspect, the invention generally relates to a method for generating x-ray images of breasts of a subject. The method includes: (1) providing a support for positioning a right and a left breast of the subject; (2) providing two arrays of x-ray sources, a right array and a left array positioned to image the right breast and the left breast, respectively, wherein the x-ray sources of each of the two arrays are arranged along a pre-defined trajectory; (3) positioning an x-ray detector between the right and left breasts configured to allow an x-ray beam generated by the right or the left array of x-ray sources to pass through the right or the left breast of the subject and to project onto a detecting surface of the x-ray detector; (4) imaging the right or the left breast to register one or more images on the x-ray detector; (5) positioning an x-ray detector between the left and right breasts configured to allow an x-ray beam generated by the left or the right array of x-ray sources to pass through the left or the right breast of the subject and to project onto a detecting surface of the x-ray detector; and (6) imaging the left or the right breast to register one or more images on the x-ray detector.

In some embodiments, the x-ray detector is angularly displaced to track the individual x-ray source of the x-ray source array.

In some embodiments, the x-ray source and the x-ray detector remain stationary when taking the one or more images of the right breast and remain stationary when taking the one or more images of the left breast.

In some embodiments, the x-ray detector remain stationary and the x-ray source travels along a pre-defined trajectory when taking the one or more images of the right breast and remain stationary when taking the one or more images of the left breast.

In some embodiments, the method further includes administering x-ray contrast agent to the subject prior to imaging.

In yet another aspect, the invention generally relates to a method for generating x-ray images of breasts of a subject. The method includes: (1) providing a support for positioning a right and a left breast of the subject; (2) providing two x-ray sources, a right and a left positioned to image the right breast and the left breast, respectively; (3) positioning an x-ray detector between the right and left breasts configured to allow an x-ray beam generated by the right or the left x-ray source to pass through the right or the left breast of the subject and to project onto a detecting surface of the x-ray detector, to register one or more images of the right or the left breast; (4) positioning the x-ray detector is relative to the right or left breast to allow the registration of one or more images thereof; (5) imaging the right or the left breast to register one or more images on the x-ray detector; (6) positioning the x-ray detector is relative to the left or right breast to allow the registration of one or more images thereof; and (7) imaging the left or the right breast to register one or more images on the x-ray detector.

In some embodiments, the x-ray detector is angularly displaced to track the individual x-ray source of the x-ray source array.

In some embodiments, the method further includes administering x-ray contrast agent to the subject prior to imaging.

In yet another aspect, the invention generally relates to a method for generating x-ray images of breasts of a subject. The method includes: (1) providing a support for positioning a right and a left breast of the subject; (2) providing an assembly of an x-ray source and an x-ray detector positioned on opposite sides of a breast of the subject to be imaged and configured to allow an x-ray beam generated by the x-ray source to pass through a breast of the subject and to project onto a detecting surface of the x-ray detector; (3) positioning the assembly of the x-ray source and the x-ray detector relative to one breast to allow the registration of one or more images thereof; (4) imaging the breast to register one or more images on the x-ray detector; (5) positioning the assembly of the x-ray source and the x-ray detector relative to the other breast to allow registration of one or more images of the other breast; and (6) imaging the other breast to register one or more images on the x-ray detector.

In some embodiments, the assembly of the x-ray source and the x-ray detector is rotatable around an axis located within the breast being imaged and normal to the subject's chest, and is translationally moveable (i.e., moveable by translation) along the said axis.

In some embodiments, the assembly of the x-ray source and the x-ray detector is rotatable around an axis located between and below the subject's breasts and normal to the subject's chest.

In some embodiments, the assembly of the x-ray source and the x-ray detector is rotatable around an axis located between and above the subject's breasts and normal to the subject's chest.

In some embodiments, the x-ray detector is angularly displaced to track the individual x-ray source of the x-ray source array.

In some embodiments, the method further includes administering x-ray contrast agent to the subject prior to imaging.

Depending on the application, suitable x-ray sources include those designed for mammography, radiography and fluoroscopy. Suitable arrays of x-ray sources may include multiple x-ray tubes, field emission x-ray sources including those based on carbon or titanium nanotubes, or a combination thereof.

Importantly, it is noted that embodiments of the invention also include those where a dual-side x-ray detector is used. Such detectors may be constructed and are commercially available. In essence, a dual-side detector can detect and record irradiation from two/both sides of the detector. Such detector obviates the need for repositioning the detector for imaging each breast (e.g., translational movement and/or flipping of the detector after one breast is imaged and before the imaging of the second breast takes place). In the case of two sets of x-ray sources directable to both breasts, a dual-side detector can allow for imaging both breasts without repositioning the detector, facilitating improved temporal resolution and shorter duration of exam. While each side of such a detector may have slightly different resolution, this can difference can be addressed and corrected by proper calibration and software-based techniques. Thus, for each embodiment disclosed herein where a single-side detector is illustrated or employed, a corresponding embodiment where a dual-side detector is used constitutes an embodiment of the present invention.

Suitable x-ray detectors include energy-integrating detectors and photon-counting detectors. Examples of energy integrating detectors include indirect conversion type detectors such as scintillator coupled amorphous silicon, scintillator complementary metal oxide semiconductor (CMOS), and scintillator coupled charge-coupled devices (CCDs) or direct conversion type detectors such as those based on amorphous selenium, mercuric iodide or lead iodide.

Examples of photon counting detectors include those based on silicon, cadmium telluride (CdTe), or cadmium zinc telluride (CZT). Many of these detectors such as scintillator coupled amorphous silicon and direct conversion selenium detectors are commercially available from various manufacturers. These detectors may be of the type of amorphous silicon x-ray detectors such as those currently manufactured by General Electric, Varian, Samsung and others. Amorphous selenium detectors have been manufactured by Hologic, Inc, and Toshiba. Photon counting detectors have been manufactured by General Electric, eV products and Medipix. Other categories of x-ray detectors are avalanche amplified flat panel detectors.

In one embodiment, a special detector can be used where the x-ray beam can enter from the position sensing array of detectors (pixels) then detected by the scintillator as described in U.S. Pat. No. 5,864,146 by Karellas, U.S. Pat. No. 6,717,174 B2 by Karellas, and U.S. Pat. No. 6,895,077 B2 by Karellas et al. Alternatively, the x-ray beam may enter the detector from both sides, first through the scintillator followed by passing through the position sensing array of detectors.

It is noted that the invention includes embodiments where different x-ray projections are employed for the right and left breast depending on the need.

While certain embodiments of the detector are flat (as schematically illustrated in the exemplary embodiments). Other embodiments include those where the detector adopts a curved shape.

In certain embodiments, images may be acquired by using two opposed x-ray sources or arrays of x-ray sources along with a rotatable detector. It is noted that two detectors can be used back to back with the repositioned x-ray sources or array sources as shown above.

The invention also includes embodiments where a single detector is used, which is capable of detecting irradiation from both sides using two x-ray sources or a single source that is capable of being repositioned 180 degrees.

Depending on the application, the systems and methods of the invention may be adapted to meet the unique requirements at hand. In some embodiments, the system or method is configured to allow imaging of the subject to take place while the subject is prone postured. In some embodiments of the systems disclosed herein, the system or method is configured to allow imaging of the subject to take place while the subject is upright postured.

Systems and methods of the invention are useful for radiographic or mammographic imaging. In some embodiments, the systems or methods are useful for radiographic or mammographic imaging with x-ray contrast agent administered to the subject prior to imaging. In some embodiments, the system is useful for radiographic or mammographic imaging without x-ray contrast agent administered to the subject prior to imaging.

Systems and methods of the invention are useful for tomographic imaging. In some embodiments, the systems or methods are useful for tomographic imaging with x-ray contrast agent administered to the patient prior to imaging. In some embodiments, the system is useful for tomographic imaging without x-ray contrast agent administered to the patient prior to imaging.

Systems and methods of the invention are useful for and can be readily adapted to perform x-ray fluorescence imaging of the breast. In such embodiments of the invention, the breast is irradiated with the x-ray beam after a contrast agent is administered (e.g., injected intravenously). X-rays from the x-ray beam interact with atoms of the contrast agent (e.g., iodinated agents or gadolinium agents). In response to the external x-ray beam stimulation atoms of the contrast medium emit characteristic x-rays, a process called x-ray fluorescence imaging (XRFI). These x-rays are detected by a detector (e.g., special photon counting detector and collimator) and the signals and images are processed and analyzed.

Thus, it is noted that for each embodiment disclosed herein referring to x-ray imaging, a corresponding embodiment where x-ray fluorescence imaging is the mode of imaging acquisition and analysis constitutes an embodiment of the present invention.

In this specification and the appended claims, the singular forms "a," "an," and "the" include plural reference, unless the context clearly dictates otherwise.

Unless defined otherwise, all technical and scientific terms used herein have the same meaning as commonly understood by one of ordinary skill in the art. Although any methods and materials similar or equivalent to those described herein can also be used in the practice or testing of the present disclosure, the preferred methods and materials are now described. Methods recited herein may be carried out in any order that is logically possible, in addition to a particular order disclosed.

INCORPORATION BY REFERENCE

References and citations to other documents, such as patents, patent applications, patent publications, journals, books, papers, web contents, have been made in this disclosure. All such documents are hereby incorporated herein by reference in their entirety for all purposes. Any material, or portion thereof, that is said to be incorporated by reference herein, but which conflicts with existing definitions, statements, or other disclosure material explicitly set forth herein is only incorporated to the extent that no conflict arises between that incorporated material and the present disclosure material. In the event of a conflict, the conflict is to be resolved in favor of the present disclosure as the preferred disclosure.

EQUIVALENTS

The representative examples are intended to help illustrate the invention, and are not intended to, nor should they be construed to, limit the scope of the invention. Indeed, various modifications of the invention and many further embodiments thereof, in addition to those shown and described herein, will become apparent to those skilled in the art from the full contents of this document, including the examples and the references to the scientific and patent literature included herein. The examples contain important additional information, exemplification and guidance that can be adapted to the practice of this invention in its various embodiments and equivalents thereof.

What is claimed is:

1. A system for generating x-ray images of breasts of a subject, comprising
   a support for positioning a right and a left breast of the subject;
   an assembly of an x-ray source and an x-ray detector, wherein
      the x-ray source and the x-ray detector are configured to allow an x-ray beam generated by the x-ray source to pass through the right or the left breast of the subject and to project onto a detecting surface of the x-ray detector, positioned between the right and left breasts, to register one or more images of the right or the left breast;

the assembly of the x-ray source and the x-ray detector is rotatable in synchrony around an axis located between the right and left breasts and substantially normal to the subject's chest, and is translatable in one or more dimensions relative to the subject's chest;

a controller unit coupled to and command the operation of the x-ray source and the x-ray detector assembly; and a computation unit configured to receive, analyze, display and/or store the one or more images of the right or the left breast, wherein the assembly of the x-ray source and the x-ray detector is first positioned relative to one breast to allow the registration of one or more images thereof and is then positioned relative to the other breast to allow registration of one or more images of the other breast.

2. The system of claim 1, wherein the x-ray source and the x-ray detector remain stationary when taking the one or more images of the right breast and remain stationary when taking the one or more images of the left breast.

3. The system of claim 2, useful for radiographic or mammographic imaging without x-ray contrast agent administered to the subject prior to imaging.

4. The system of claim 2, useful for radiographic or mammographic imaging with x-ray contrast agent administered to the subject prior to imaging.

5. The system of claim 1, wherein the x-ray detector remains stationary and the x-ray source travels along a pre-defined trajectory when taking the one or more images of the right breast and the x-ray detector remains stationary and the x-ray source travels along a pre-defined trajectory when taking the one or more images of the left breast.

6. The system of claim 5, useful for tomographic imaging with x-ray contrast agent administered to the patient prior to imaging.

7. The system of claim 5, useful for tomographic imaging without x-ray contrast agent administered to the patient prior to imaging.

8. The system of claim 1, configured to allow imaging of the subject to take place while the subject is in a prone posture.

9. The system of claim 1, configured to allow imaging of the subject to take place while the subject is in an upright posture.

10. The system of claim 1, wherein the assembly of the x-ray source and the x-ray detector is rotatable in synchrony around an axis located substantially mid-way between the right and left breasts and normal to the subject's chest.

11. A system for generating x-ray images of breasts of a subject, comprising a support for positioning a right and a left breast of the subject;

two arrays of x-ray sources, a right array and a left array positioned to image the right breast and the left breast, respectively, wherein the x-ray sources of each of the two arrays are arranged along a pre-defined trajectory;

an x-ray detector, positioned between the right and left breasts, configured to allow an x-ray beam generated by the right or the left array of x-ray sources to pass through the right or the left breast of the subject and to project onto a detecting surface of the x-ray detector to register one or more images of the right or the left breast;

a controller unit coupled to and command the operation of the x-ray detector; and a computation unit configured to receive, analyze, display and/or store the one or more images of the right or the left breast, wherein the x-ray detector is rotatable around an axis located between the right and left breasts and normal to the subject's chest, and is translatable in one or more dimensions relative to the subject's chest; and the x-ray detector is first positioned relative to one breast to allow the registration of one or more images thereof and is then positioned relative to the other breast to allow registration of one or more images of the other breast.

12. The system of claim 11, configured to allow imaging of the subject while the subject is in a prone posture.

13. The system of claim 11, configured to allow imaging of the subject while the subject is in an upright posture.

14. The system of claim 11, wherein the two arrays of x-ray sources remain stationary during imaging.

15. The system of claim 11, wherein the x-ray detector is angularly displaced such that it tracks the individual x-ray source of the x-ray source array.

16. The system of claim 11, useful for radiographic or mammographic imaging with x-ray contrast agent administered to the subject prior to imaging.

17. The system of claim 11, useful for radiographic or mammographic imaging without x-ray contrast agent administered to the subject prior to imaging.

18. The system of claim 11, useful for tomographic imaging with x-ray contrast agent administered to the patient prior to imaging.

19. The system of claim 11, useful for tomographic imaging without x-ray contrast agent administered to the patient prior to imaging.

20. A method for generating x-ray images of breasts of a subject, comprising providing a support for positioning a right and a left breast of the subject;

providing an assembly of an x-ray source and an x-ray detector, wherein the x-ray source and the x-ray detector are configured to allow an x-ray beam generated by the x-ray source to pass through the right or the left breast of the subject and to project onto a detecting surface of the x-ray detector, positioned between the right and left breasts, to register one or more images of the right or the left breast;

the assembly of the x-ray source and the x-ray detector is rotatable in synchrony around an axis located between the right and left breasts and normal to the subject's chest, and is translatable in one or more dimensions relative to the subject's chest;

positioning the assembly of the x-ray source and the x-ray detector relative to one breast to allow the registration of one or more images thereof;

imaging the breast to register one or more images on the x-ray detector;

positioning the assembly of the x-ray source and the x-ray detector relative to the other breast to allow registration of one or more images of the other breast; and imaging the other breast to register one or more images on the x-ray detector.

* * * * *

UNITED STATES PATENT AND TRADEMARK OFFICE
CERTIFICATE OF CORRECTION

| | |
|---|---|
| PATENT NO. | : 9,629,597 B2 |
| APPLICATION NO. | : 14/772227 |
| DATED | : April 25, 2017 |
| INVENTOR(S) | : Vedantham |

It is certified that error appears in the above-identified patent and that said Letters Patent is hereby corrected as shown below:

In the Specification

Column 1, Line 16 the section title "STATEMENT REGARDING FEDERALLY FUNDED RESEARCH OR DEVELOPMENT" and the paragraph that immediately follows it should read:

Statement Regarding Federally Funded Research
This invention was made with government support under Grant Numbers CA134128 and CA128906 awarded by the National Institutes of Health. The Government has certain rights in the invention.

Signed and Sealed this
Thirtieth Day of May, 2017

Michelle K. Lee
*Director of the United States Patent and Trademark Office*